United States Patent
Kovacs et al.

(10) Patent No.: US 9,480,966 B2
(45) Date of Patent: *Nov. 1, 2016

(54) SUBSTRATES AND METHODS FOR COLLECTION, STABILIZATION AND ELUTION OF BIOMOLECULES

(71) Applicant: General Electric Company, Schenectady, NY (US)

(72) Inventors: Ernest William Kovacs, Cohoes, NY (US); Erik Leeming Kvam, Niskayuna, NY (US); Bing Li, Clifton Park, NY (US); Frank John Mondello, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 106 days.

This patent is subject to a terminal disclaimer.

(21) Appl. No.: 14/261,900

(22) Filed: Apr. 25, 2014

(65) Prior Publication Data

US 2014/0234942 A1 Aug. 21, 2014

Related U.S. Application Data

(63) Continuation-in-part of application No. 13/460,076, filed on Apr. 30, 2012, now Pat. No. 9,044,738, and a continuation-in-part of application No. 13/721,948, filed on Dec. 20, 2012, now Pat. No. 9,040,675, and a continuation-in-part of application No. 13/968,497, filed on Aug. 16, 2013, now Pat. No. 9,040,679.

(51) Int. Cl.
| | |
|---|---|
| *B01J 20/22* | (2006.01) |
| *B01J 20/24* | (2006.01) |
| *C07K 1/14* | (2006.01) |
| *C12N 15/10* | (2006.01) |
| *B01J 20/28* | (2006.01) |
| *B01J 20/32* | (2006.01) |

(52) U.S. Cl.
CPC .............. *B01J 20/22* (2013.01); *B01J 20/24* (2013.01); *B01J 20/28033* (2013.01); *B01J 20/3212* (2013.01); *B01J 20/3242* (2013.01); *B01J 20/3246* (2013.01); *C07K 1/145* (2013.01); *C12N 15/1006* (2013.01); *C12N 15/1017* (2013.01)

(58) Field of Classification Search
CPC ...... B01J 20/22; B01J 20/24; B01J 20/3246; B01J 20/28033; B01J 20/3212; B01J 20/3242; C07K 1/145; C12N 15/1006; C12N 15/1017
USPC ............. 435/207; 502/4, 404; 530/351, 359, 530/412; 536/123.1, 24.41
See application file for complete search history.

(56) References Cited

U.S. PATENT DOCUMENTS

| | | | |
|---|---|---|---|
| 4,540,506 A | 9/1985 | Jacobson et al. | |
| 5,173,422 A | 12/1992 | Knowles et al. | |
| 5,496,562 A | 3/1996 | Burgoyne | |
| 5,593,824 A * | 1/1997 | Treml ...................... | C12Q 1/68 424/484 |
| 5,756,126 A | 5/1998 | Burgoyne et al. | |
| 5,807,527 A | 9/1998 | Burgoyne | |
| 5,939,259 A | 8/1999 | Harvey et al. | |
| 5,981,218 A | 11/1999 | Rio et al. | |
| 6,004,574 A * | 12/1999 | Backstrom ........... | A61K 9/0075 424/434 |
| 6,168,922 B1 | 1/2001 | Harvey et al. | |
| 6,294,203 B1 | 9/2001 | Burgoyne | |
| 6,528,641 B2 | 3/2003 | Lader | |
| 6,602,718 B1 | 8/2003 | Augello et al. | |
| 6,776,959 B1 | 8/2004 | Helftenbein | |
| 6,794,140 B1 | 9/2004 | Goldsborough | |
| 6,867,290 B2 | 3/2005 | Goldsborough | |
| 7,163,793 B2 | 1/2007 | Kudlicki et al. | |
| 7,244,568 B2 | 7/2007 | Goldsborough | |
| 7,250,270 B2 | 7/2007 | Goldrick et al. | |
| 7,282,371 B2 | 10/2007 | Helftenbein | |
| 7,589,184 B2 | 9/2009 | Hogan et al. | |
| 8,025,850 B2 | 9/2011 | Chan | |
| 8,048,681 B2 | 11/2011 | Yamashita et al. | |
| 8,088,576 B2 | 1/2012 | Gumbrecht et al. | |
| 8,158,357 B2 | 4/2012 | Birnboim et al. | |
| 2001/0039010 A1 | 11/2001 | Burgoyne | |
| 2002/0146696 A1 | 10/2002 | Burgoyne | |
| 2003/0134312 A1 | 7/2003 | Burgoyne | |
| 2003/0143566 A1 | 7/2003 | Helftenbein | |
| 2004/0009496 A1 | 1/2004 | Eiblmaier et al. | |

(Continued)

FOREIGN PATENT DOCUMENTS

| | | |
|---|---|---|
| CN | 101878304 A | 11/2010 |
| CN | 103173432 A | 6/2013 |

(Continued)

OTHER PUBLICATIONS

Search Report and Written Opinion from PCT Application No. PCT/US2013/38576 dated Sep. 6, 2013.

(Continued)

*Primary Examiner* — Ganapathy Krishnan

(74) *Attorney, Agent, or Firm* — Eileen B. Gallagher

(57) ABSTRACT

A solid substrate for the extraction, stabilization, and storage of proteins is provided. The substrate includes: a polysaccharide, such as melezitose under a substantially dry state. The substrate is configured to extract proteins from a sample and stabilize the extracted proteins in a dry format under ambient conditions for a prolonged period of time. Methods for collecting and recovering the proteins stored in the dry solid substrate are also described.

15 Claims, 1 Drawing Sheet

(56) References Cited

U.S. PATENT DOCUMENTS

| | | |
|---|---|---|
| 2004/0126783 A1 | 7/2004 | Bortolin et al. |
| 2005/0123965 A1* | 6/2005 | Yamashita ............ C12N 15/101 435/6.16 |
| 2006/0099567 A1 | 5/2006 | Muller-Cohn et al. |
| 2006/0147918 A1 | 7/2006 | Goldsborough |
| 2007/0117173 A1 | 5/2007 | Levison et al. |
| 2008/0176209 A1 | 7/2008 | Muller et al. |
| 2008/0262097 A1 | 10/2008 | Eady et al. |
| 2009/0053704 A1 | 2/2009 | Novoradovskaya et al. |
| 2009/0143570 A1 | 6/2009 | Jiang et al. |
| 2009/0162924 A1 | 6/2009 | Birnboim |
| 2009/0208919 A1 | 8/2009 | Utermohlen et al. |
| 2009/0246750 A1 | 10/2009 | Lloyd et al. |
| 2009/0291427 A1 | 11/2009 | Muller-Cohn et al. |
| 2010/0173392 A1 | 7/2010 | Davis et al. |
| 2010/0209957 A1 | 8/2010 | Hogan et al. |
| 2010/0248363 A1 | 9/2010 | Hogan et al. |
| 2011/0054157 A1 | 3/2011 | Bitner |
| 2011/0070585 A1 | 3/2011 | Ollikka et al. |
| 2011/0081363 A1* | 4/2011 | Whitney .................. A01N 1/00 424/184.1 |
| 2012/0052572 A1 | 3/2012 | Whitney et al. |
| 2012/0059160 A1 | 3/2012 | Bitner et al. |
| 2012/0152743 A1 | 6/2012 | Finehout et al. |
| 2012/0237939 A1 | 9/2012 | Reed et al. |
| 2013/0289257 A1 | 10/2013 | Bales et al. |
| 2015/0118683 A1 | 4/2015 | Li et al. |
| 2015/0119566 A1 | 4/2015 | Li et al. |
| 2015/0299693 A1 | 10/2015 | Chen et al. |

FOREIGN PATENT DOCUMENTS

| | | | |
|---|---|---|---|
| EP | 1484111 A1 | 12/2004 | |
| EP | 1559784 A2 | 8/2005 | |
| EP | 2388312 A1 | 11/2011 | |
| WO | 9118091 A1 | 11/1991 | |
| WO | WO 91/18091 * | 11/1991 | ............ C12N 9/96 |
| WO | 00/66606 A1 | 11/2000 | |
| WO | 03020924 A2 | 3/2003 | |
| WO | 03086443 A1 | 10/2003 | |
| WO | 2007008722 A2 | 1/2007 | |
| WO | 2009029433 A2 | 3/2009 | |
| WO | 2010132508 A2 | 11/2010 | |
| WO | 2010144682 A1 | 12/2010 | |
| WO | WO2010/144682 * | 12/2010 | ............ C12N 9/96 |
| WO | 2011131720 A1 | 10/2011 | |
| WO | WO 2011/131720 A1 * | 10/2011 | ............ C12N 9/54 |
| WO | 2012075471 A1 | 6/2012 | |
| WO | 2012113907 A2 | 8/2012 | |
| WO | 2012113911 A1 | 8/2012 | |
| WO | 2013066249 A1 | 5/2013 | |
| WO | 2015162093 A1 | 10/2015 | |

OTHER PUBLICATIONS

Natarajan, et al. "Paper-based archiving of mammalian and plant samples for RNA analysis" BioTechniques, 2000, 29 pp. 1328-1333.

Tan, et al., "DNA, RNA, and Protein Extraction: The Past and the Present", Journal of Biomedicine and Biotechnology, 2009, pp. 1-10.

Kumar et al. "Inhibition of mammalian ribonucleases by endogenous adenosine dinucleotides", 2003 Biochemical and Biophysical Research Communications 300, pp. 81-86.

Cline, et al. "New Water-Soluble Phosphines as Reductants of Peptide and Protein Disulfide Bonds: Reactivity and Membrane Permeability" 2004 Biochemistry 43: pp. 15195-15203.

Search Report and Written Opinion from PCT Application No. PCT/US2013/065821 dated Jan. 29, 2014.

Li, et al, "Kinetics of RNA degradation by specific base catalysis of transesterification involving the 2'-hydroxyl group" Journal American Chemistry Society, 1999, 121 (23) pp. 5364-5372.

Zale, et al. "Why does ribonuclease irreversibly inactivate at high temperatures?", Biochemistry, 1986, 25 (19) pp. 5432-5444.

Matsubara, et al., "Dried blood spot on filter paper as a source of mRNA", Nucleic Acids Research, vol. 20, Issue 8, Apr. 25, 1992, p. 1998 1 Page.

Sambrook, J. et al. "Molecular Cloning: a Laboratory Manual, 2nd edition" Cold Spring Harbor, New York, Cold Spring Harbor Laboratory Press, Dec. 1989, vol. 1, pp. 7.2, 7.3, 7.4 and 7.5.

Zhang et al., "RNA analysis from newborn screening dried blood specimens", Human Genetics, vol. 89, Issue 3, May 1992, pp. 311-314.

Supplementary European Search Report from EP Application No. 13784927.9 dated Jan. 29, 2015.

Ambion, "RNAqueous TM-4PCR Instruction Manual Passage", RNAqueous TM-4PCR Instruction Manual, US, Apr. 18, 2002, pp. 1-29.

Ambion Technotes, "Maximize your RNA yield: What Yield to expect", vol. 8, No. 3, May 18, 2001 pp. 1, 13-14, I.

Search Report and Written Opinion from PCT Application No. PCT/EP2014/067453 dated Dec. 19, 2014.

Mollmann et al., "The stability of insulin in solid formulations containing melezitose and starch. Effect of processing and excipeients", Drug Development and Industrial Pharmacy, vol. 32, No. 6, Jun. 1, 2006, 7 Pages.

Search report and Written Opinion for corresponding PCT application EP2015/058518 issued on Jun. 19, 2015, 9 Pages.

Office Action for corresponding CN application No. 201380022584.6 issued on Jul. 17, 2015, 18 Pages.

* cited by examiner

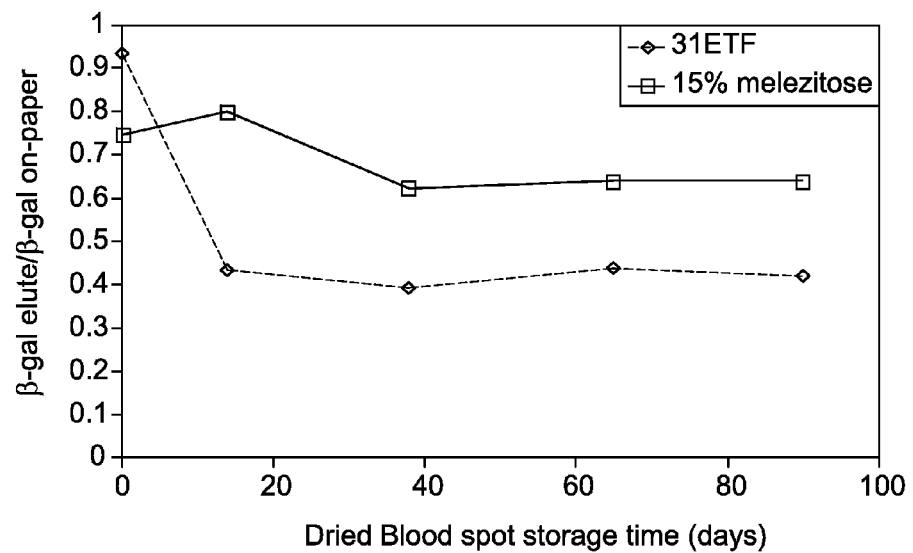

SUBSTRATES AND METHODS FOR COLLECTION, STABILIZATION AND ELUTION OF BIOMOLECULES

CROSS REFERENCE TO RELATED APPLICATIONS

This application is a continuation-in-part of U.S. patent application Ser. No. 13/460,076 entitled "Methods and compositions for extraction and storage of nucleic acids", filed Apr. 30, 2012; U.S. patent application Ser. No. 13/721,948 entitled "Formulations for nucleic acid stabilization on solid substrates", filed Dec. 20, 2012; and U.S. patent application Ser. No. 13/968,497 entitled "Methods and Compositions For Extraction and Storage of Nucleic Acids", filed Aug. 16, 2013; which are herein incorporated by reference.

FEDERALLY SPONSORED RESEARCH & DEVELOPMENT

This invention was made with Government support under contract number HR0011-11-C0127 awarded by the Defense Advanced Research Projects Agency. The Government has certain rights in the invention.

FIELD

The invention relates to dry solid substrates for collection, stabilization and elution of biomolecules from a biological sample. The invention further relates to methods for collection, stabilization and elution of biomolecules from a biological sample from the dry solid substrates.

BACKGROUND

Preserving the structural and functional integrity of biomolecules during isolation or purification from a biological sample is essential for various downstream applications including analyte detection, sensing, forensic, diagnostic or therapeutic applications, and the like. The extraction and stabilization of proteins, peptides or amino acids derived from a biological sample are sensitive to a number of environmental factors including, but are not limited to, solution pH, temperature, and the ubiquitous presence of various proteases. Consequently, proteins or peptides in solution states are typically stored under refrigeration (e.g. 4° C., −20° C., or −80° C.) to prevent hydrolysis and enzymatic degradation and to preserve the integrity of protein structure or function.

Dry-state technologies claiming successful collection and preservation of proteins or peptides in dry formats typically require protein to be "pre-purified" and "concentrated" from a sample prior to storage. Other dry-state technologies for the preservation of proteins in dry formats require additional drying facilities (e.g. forced air flow, lyophilization). These methods are therefore not conducive to direct collection and stabilization of proteins or peptides from a sample (e.g., a biological sample) without additional and significant processing steps.

Proteins or peptides are prone to denaturation and consequently tend to lose biological activity or epitope recognition during storage. Proteins that are targets of different analytical tests, such as biomarkers or biological therapeutic drugs, may be present in low quantities in unpurified states. Thus, methods for maximizing the recovery of protein analytes of interest are highly desirable. Degradation of protein or peptide may be slowed or prevented using chemical additives that, for example, inhibit protease activity. However, the presence of chemical additives may affect down-stream analytical techniques including mass spectroscopy and immunoassays.

Untreated cellulose paper substrates, such as, 903 or 31ETF papers (Whatman™, GE Healthcare) or Grade 226 paper (Ahlstrom, PerkinElmer) are used widely for preservation of enzymes, antibodies, proteins, peptides, and amino acids in dried blood spots for analytical purposes such as neonatal testing. However, the recovery of analytes from untreated cellulose substrates and subsequent biological activity of said analytes, particularly proteins that are prone to degradation, are often not sufficient. Dried specimens, such as dried blood spot samples used in neonatal testing, are generally stored under refrigeration to maintain analyte stability. Analytes which can be eluted inefficiently from dried blood spots may be interpreted in the art as unstable targets due to poor functional recovery. Supplementing different chemical fillers to stabilize proteins has been reported in the art, however the fillers have limited ability to recover and stabilize sensitive proteins.

Accordingly, compositions and methods which enable collection and extraction of biomolecules including proteins, peptides or amino acids from a biological sample, and then stabilize the biomolecules under a dry-state and ambient conditions without pre-purification, and elute the biomolecules in a substantially intact form thereafter for further analysis are highly desirable.

BRIEF DESCRIPTION

One embodiment of a solid substrate for extraction, stabilization and elution of biomolecules, comprises a melezitose under a substantially dry state.

In another embodiment, a solid substrate for collection, stabilization and elution of biomolecules, comprises a trisaccharide under a substantially dry state.

One example of a method for extracting, stabilizing and eluting biomolecules from a biological sample disposed on a solid substrate, comprises contacting the biological sample to the substrate; drying the biological sample to a substantially dry state; and eluting the biomolecules from the biological sample dried on the substrate by rehydrating the substrate in an elution buffer, wherein the solid substrate comprises melezitose under a substantially dry state, and optionally one or more lysis reagents, nucleic acid denaturing reagents or combinations thereof, impregnated therein under a substantially dry state.

BRIEF DESCRIPTION OF DRAWING

FIG. 1 is a graph showing enhanced elution efficiency of active, non-denatured β-gal while recovered from a substrate with 15% melezitose compared to unmodified 31-ETF cellulose.

DETAILED DESCRIPTION

The embodiments provide suitable matrices and methods for extraction, stabilization and elution of biomolecules, such as proteins, peptides, amino acids, enzymes, and antibodies. Biomolecules which are prone to denaturation are therefore difficult to preserve in an intact form. One or more embodiments of the invention relate to a solid substrate for extraction, stabilization and elution of biomolecules, wherein the substrate comprises a trisaccharide, such as melezitose under a substantially dry state. The solid substrate is configured to collect a biological sample, then extract and stabilize proteins, peptides or amino acids from the sample for a prolonged period, followed by elution within a single process step. The eluted proteins or peptides are used in various downstream applications. The substrate is configured to stabilize proteins or peptides in a substantially dry-state at ambient temperature and substantially retain the integral structure and/or function of the protein.

To more clearly and concisely describe the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

The term "biological sample" as referred to herein includes, but is not limited to, blood, serum, tissue, and saliva obtained from any organism, including a human. Biological samples may be obtained by an individual undergoing a self-diagnostic test (e.g., blood glucose monitoring) or by a trained medical professional through a variety of techniques including, for example, aspirating blood using a needle or scraping or swabbing a particular area, such as a lesion on a patient's skin. Methods for collecting various biological samples are well known in the art. The term "sample" includes biological samples as defined above, but also includes, for example, tissue cultured cells and purified proteins.

The term, "reducing agents" as referred to herein include any chemical species that provides electrons to another chemical species. A variety of reducing agents are known in the art. Exemplary reducing agents include dithiothreitol (DTT), 2-mercaptoethanol (2-ME), and tris(2-carboxyethyl) phosphine (TCEP). Moreover, any combination of these or other reducing agents may be used. In particular embodiments, the reducing agent is TCEP.

The term "buffer" as used herein includes, for example, 2-Amino-2-hydroxymethyl-propane-1,3-diol (Tris), 2-(N-morpholino) ethanesulfonic acid (MES), 3-(N-morpholino) propanesulfonic acid (MOPS), citrate buffers, 4-(2-hydroxyethyl)-1-piperazineethanesulfonic acid (HEPES), and phosphate buffers. This list of potential buffers is for illustrative purposes only. The pH of the buffer selected for use in the compositions and methods disclosed herein is typically in the range of 3 to 10. In some embodiments, the pH of the buffer used herein is in a range of 6 to 9, or in some other embodiments, the pH of the buffer is in a range of 7 to 8.

One embodiment of a solid substrate for collection, stabilization and elution of biomolecules, comprises a trisaccharide under a substantially dry state. The trisaccharide may be selected from melezitose, raffinose, maltotriulose, isomaltotriose, nigerotriose, maltotriose, ketose or combinations thereof.

One or more embodiments of a solid substrate comprise a melezitose under a substantially dry state. Melezitose is a non-reducing trisaccharide sugar, having a molecular weight of 504, 44 g/mol. In one or more embodiments, the solid substrate comprises melezitose, wherein a concentration of the melezitose is in range of about 10 to 30%. In one embodiment, the concentration of melezitose is 15%. The melezitose may be impregnated in the substrate. In some embodiments, the impregnated melezitose concentration in the substrate is between 10 to 30%. In some other embodiments, 15% melezitose is impregnated in the substrate. The substrate may be passively coated or covalently-modified with melezitose. In some other embodiments, the substrate is coated with a 15% solution of melezitose. The substrate with melezitose has shown high stability of the proteins, as well as provide higher yield, as described in Example 2.

In one or more examples, the substrate is further impregnated with one or more reagents, such as lysis reagents, buffer reagents or reducing agents. In some embodiments, the impregnated reagents comprise cell lytic reagents, biomolecule stabilizing reagents such as protein-stabilizing reagents, protein storage chemicals and combinations thereof impregnated therein under a substantially dry state.

The substrate is also configured to extract proteins or peptides from a biological sample and preserve that in a substantially dry state at ambient temperature. As used herein, the term "substantially dry state" refers to drying the extracted biomolecules to have approximately less than 2% of water content. Similarly, the reagents are impregnated in the substrate in a substantially dry state.

"Incorporation" of the compositions into the substrate includes, but is not limited to, the "dipping" procedure described below. In some embodiments, such methods accomplish incorporation of the composition into the dry solid substrate. Following incorporation of the composition into the dry solid substrate, the solid substrate is dried using any appropriate method.

In one or more embodiments, the substrate comprises lysis reagents. The lysis reagents may comprise detergents, chaotropes, denaturants or combinations thereof. Without intending to be limited to a particular denaturant, it may be categorized as either weak or strong lytic reagents depending on their biophysical properties and ability to completely inhibit biological enzyme activity (e.g. proteases). In some embodiments, weak protein denaturants (e.g. detergent) may be used for lysing cells and disrupting protein-protein interactions without denaturing proteins. Numerous lysis reagents are known in the art and may be selected for use in the compositions and methods described herein. Without intending to be limited to a particular lysis reagents, exemplary lysis reagents include guanidinium thiocyanate, guanidinium hydrochloride, sodium thiocyanate, potassium thiocyanate, arginine, sodium dodecyl sulfate (SDS), urea or a combination thereof.

As noted, the lysis reagents may include detergents, wherein exemplary detergents may be categorized as ionic detergents, non-ionic detergents, or zwitterionic detergents. The ionic detergent may comprise anionic detergent such as, sodium dodecylsulphate (SDS) or cationic detergent, such as ethyl trimethyl ammonium bromide. Non-limiting examples of non-ionic detergent for cell lysis include TritonX-100, NP-40, Brij 35, Tween 20, Octyl glucoside, Octyl thioglucoside or digitonin. Some zwitterionic detergents may comprise 3-[(3-Cholamidopropyl)dimethylammonio]-1-propanesulfonate (CHAPS) and 3-[(3-Cholamidopropyl) dimethylammonio]-2-hydroxy-1-propanesulfonate (CHAPSO).

In one or more embodiments, the lysis reagent comprises a thiocyanate salt. One or more embodiments of the substrate comprises a thiocyanate salt impregnated in a dry state. Exemplary thiocyanate salts include, but are not limited to, guanidinium thiocyanate, sodium thiocyanate, potassium thiocyanate or combinations thereof. In some other embodiments, the lysis reagent is selected from guanidinium thiocyanate, sodium thiocyanate, sodium dodecyl sulfate (SDS) or combinations thereof.

In one or more embodiments, the substrate maintains stability and integrity of the protein at a desired level after extraction from a biological sample. In one embodiment, the substrate is impregnated with one or more protein stabilizing reagents. These stabilizing reagents may include protease inhibitors, buffer, or chelating agents (e.g EDTA).

The digestion of recovered proteins in the presence of proteases may be avoided by adding one or more protease inhibitors to the substrate, wherein the protease inhibitors may be added externally or may be impregnated in the substrate. In one embodiment, impregnated protease inhibitors may be activated upon wetting of the dry substrate. In some embodiments, the substrate further comprises a protease inhibitor, wherein the protease inhibitor is synthetic or occurs naturally (e.g. naturally-occurring peptide or protein) and comprises aprotinin, bestatin, chymostatin, leupeptin, alpha-2-macroglobulin, pepstatin, phenylmethanesulfonyl fluoride, N-ethylmaleimide, ethylenediaminetetraacetid acid, antithrombin, or combinations thereof. In one example, an addition of such protease inhibitors enhances the stability of the proteins in both liquid state and dry-formats by inhibiting the proteases or peptidases.

Certain embodiments of the substrate comprise buffer reagents in a dry-state, which may be re-hydrated during the extraction process. Examples of these buffers include, but are not limited to, 2-Amino-2-hydroxymethyl-propane-1,3-diol (Tris), 2-(N-morpholino) ethanesulfonic acid (MES), 3-(N-morpholino) propanesulfonic acid (MOPS), citrate buffers, 4-(2-hydroxyethyl)-1-piperazineethanesulfonic acid (HEPES), phosphate buffers or combinations thereof. As noted, the substrate provides a pH of 6 to 8 on hydration, which enables extraction of biomolecules from the biological samples and stabilization of the extracted biomolecules. The hydration may be achieved by adding a sample, water or any other solution (e.g. a buffer solution). One or more embodiments of the substrate provide a pH in a range from 2 to 7 on hydration. In some embodiments, the substrate provides a pH in a range from 7 to 10 on hydration. In one embodiment, the substrate provides a pH range from 6 to 8 upon hydration.

In some embodiments, the substrate further comprises at least one reducing agent, wherein the reducing agent is selected from the group consisting of dithiothreitol (DTT), 2-mercaptoethanol (2-ME), tris(2-carboxyethyl)phosphine (TCEP) and combinations thereof.

In some embodiments, the substrate comprises one or more chelating agents. The chelating agents may be selected from ethylenediaminetetraacetic acid (EDTA), citric acid, ethylene glycol tetraacetic acid (EGTA), or combinations thereof.

In some embodiments, the substrate further comprises a polysaccharide. The polysaccharide may be selected from dextran, Ficoll®, chitosan, amylopectin, alginate, carboxymethyl cellulose, or combinations thereof. In one embodiment, the polysaccharide is Ficoll®. In one embodiment, the substrate further comprises 15% solution of Illustra™ Ready-To-Go (RTG) components from GE Healthcare.

The substrate enables collection, extraction and storage of proteins or peptides without solubilizing the substrate material. The solid substrate may be selected from the group consisting of a nitrocellulose membrane, a cellulose membrane, a cellulose acetate membrane, a regenerated cellulose membrane, a nitrocellulose mixed ester membranes, a polyethersulfone membrane, a nylon membrane, a polyolefin membrane, a polyester membrane, a polycarbonate membrane, a polypropylene membrane, a polyvinylidene difluoride membrane, a polyethylene membrane, a polystyrene membrane, a polyurethane membrane, a polyphenylene oxide membrane, a poly(tetrafluoroethylene-co-hexafluoropropylene membrane, glass fiber and any combination of two or more of the above membranes.

The solid substrate may be porous. In one embodiment, the solid substrate is a porous cellulose paper, such as a cellulose substrate from Whatman™. In one example, the cellulose substrate from Whatman™ comprises 903-cellulose, FTA™ or FTA™ Elute.

As noted, the solid substrate comprises the composition in a dry state and also preserves the extracted proteins under dry conditions. The use of a dry solid substrate for extraction and storage is advantageous over liquid-based extraction, because the dry substrate ensures minimal volumetric dilution of the sample applied to the substrate. A liquid-based extraction may dilute the concentration of the sample in an excess volume of stabilizing reagent. In contrast, a dry solid substrate for extracting and stabilizing biomolecules maintains the concentration of the sample, as well as the extracted biomolecules, and eliminates issues, such as sample degradation, that are related to improper dilution of sample in an insufficient volume of liquid preservative. In addition, the solid substrate comprises a fixed composition of the dry reagents, which enables efficient extraction of biomolecules, such as proteins, peptides or amino acids upon hydration, followed by stabilization of the extracted biomolecules at ambient temperature.

The terms "ambient condition" or "ambient temperature" are interchangeably used hereinafter. As used herein, the term "ambient temperature" refers to a temperature in a range between 0° C. to 60° C. In one or more embodiments, the ambient temperature is room temperature. In some embodiments, the substrate is configured to store or preserve proteins under ambient temperature in a dried state.

As noted, the solid substrate is configured to store or preserve proteins under dry-state for prolonged period. The term "configured to" or "configured for" is referred to herein as the structure or composition of the substrate that enables the substrate to extract and store proteins for periods of time at ambient temperature. The terms "storage" or "preservation" may be interchangeably used herein with respect to maintaining the extracted proteins in a format suitable for further analysis. More specifically, the proteins may be stored or preserved in a solid substrate, wherein the substrate ensures maintaining the integrity of the molecules.

In some embodiments, the substrate is a solid phase extraction substrate. A substrate, where the solid phase extraction method is used, is referred to herein as a solid phase extraction substrate. Solid-phase extraction (SPE) technology has been leveraged to reduce the extraction times of high purity proteins for sequencing and other applications. The solid phase extraction is an extraction method that uses a solid phase and a liquid phase to isolate one or more molecules of the same type, or different types, from a material. The substrate is used, for example, to purify a sample upstream of a chromatographic separation or other analytical method.

In some examples, the substrate permits the storage of proteins, which are prone to degradation, in a dry format (e.g., on a solid substrate) at ambient temperatures. In one or more embodiments, the substrate is configured to provide improved stability and elution for biomolecules at ambient temperatures. In some embodiments, the substrate is configured to provide improved stability to the biomolecules during storage of at least one month to three months at ambient temperature between 20 to 22° C.

The substrate is configured to store proteins in a dry format at ambient temperature under substantially intact form. The term "form" of the proteins refers to the integral structure or function of the proteins.

In some embodiments, the dried reagents impregnated in the substrate are hydrated by adding a buffer, water or a sample. In one embodiment, the impregnated dried reagents are hydrated by a sample, more specifically a biological sample, which is disposed on the substrate for extraction or storage of proteins. In some other embodiments, in addition to a sample, water or buffer is added to hydrate the substrate and reconstitute or activate the reagents embedded in the substrate. In some embodiments, the hydration of the substrate generates an appropriate pH for extraction of proteins on the substrate. In some embodiments, the hydration further results in reconstituting the reagents, such as cell-lysis reagents, protein stabilizing reagents, reducing agents, buffer reagents that are present in a dried form in the substrate.

Methods for extracting, stabilizing and eluting biomolecules from a biological sample disposed on a solid substrate are provided herein. An example of a method comprises contacting the biological sample to the substrate, wherein the substrate comprises melezitose under a substantially dry state, and one or more lysis reagents, nucleic acid denaturing reagents or combinations thereof impregnated therein under a substantially dry state. Non-limiting examples of the term "contacting the biological sample" include, applying a sample or disposing a sample on the substrate using a pipet, catheter, syringe or conduit. In some embodiments, the sample may be poured onto the substrate. The method further comprises drying the biological sample to a substantially dry state. For elution, the biomolecules are eluted from the biological sample dried on the substrate by rehydrating the substrate in an elution buffer.

The term "extraction" refers to any method for separating or isolating the proteins from a sample, more particularly from a biological sample. The term "extraction" and "collection" are interchangeably used herein. Biomolecules such as proteins and peptides may be released from a cell by cell-lysis. In one embodiment, the proteins may be released during evaporative cell-lysis. In another embodiment, the cells are lysed upon contact with the substrate comprising cell lysis reagents. Contacting a biological sample comprising cells to the substrate results in cell lysis which releases proteins, for example by using FTA™ or FTA™ Elute cellulose papers.

As noted, the method further comprises drying the biological sample to a substantially dry state, wherein the dried sample may be stored on the substrate for a longer period of time. The solid substrate is dried using any appropriate method, such as air-drying or vacuum-drying. The sample dried substrate may be stored for several weeks or months, and depending on the requirement, proteins or peptides may be eluted from the dried sample on the substrate.

In one embodiment, the method further comprises storing the extracted proteins on the solid substrate in a substantially dry state at ambient temperature. In some embodiments, the proteins may be stored for more than one month time period. In some embodiments, the proteins may be stored for more than a six months period. As some of the proteins or peptides are prone to degradation, the extraction and preservation using the substrate is useful and the recovered proteins or peptides may further be used for various downstream applications.

As noted, the method further comprises eluting the biomolecules from the biological sample dried on the substrate by rehydrating the substrate in an elution buffer. The term "elution" refers to recovering the biomolecules, such as protein or peptides from the substrate by various means. One or more embodiments of the method comprise recovering the biomolecules from the substrate by solid phase extraction technique. In one or more embodiments, the proteins are eluted from the solid substrate by rehydrating the substrate in an aqueous solution, a buffer, or an organic solution, and wherein the proteins are subjected to further analysis. Any method that enables the elution of the biomolecules from a sample (e.g., an unpurified biological sample) may be employed. The proteins may be eluted by rehydrating the solid substrate (e.g., cellulose paper) in an aqueous solution, a buffer solution as defined above, or an organic solution. In some embodiments, the proteins are recovered from the solid substrate by electroelution, electrophoresis, or washing with elution buffer.

The method delineated above may optionally include a step of washing the substrate before eluting the proteins from the solid substrate for further analysis. For example, the substrate may be washed for one or more times with a suitable buffer or water prior to elution of the proteins.

In some embodiments, the substrate is configured to provide 70 to 90% recovery on elution of the biomolecules from the substrate. The elution is performed so that the biomolecules are eluted in an intact form. In embodiments of the method, the elution of biomolecules does not require pre-purification of the proteins or peptides for effective stabilization and preservation. The proteins or peptides may be extracted followed by stabilization and elution in a single step.

As noted, the proteins or peptides, which are prone to degradation on long term storage may be defined in terms of percent recovery of the protein in biologically active state. The protein that is prone to degradation is defined as, a protein which has less than about 60% recovery, or has less than about 40% recovery in a biologically active state after storage in a substrate for one week at a room temperature, wherein the substrate is devoid of any reagents.

In some embodiments, the entire method of using the substrate, such as applying the biological sample, drying the sample on the substrate, storage, extraction and elution of the proteins or peptides from the substrate may be performed under aseptic conditions.

The samples utilized in this method include, but are not limited to, biological samples such as blood, serum, tissue, and saliva obtained from any organism, including a human.

The extracted biomolecules may comprise proteins, peptides, amino acids, enzymes, antibodies, or combinations thereof. The biomolecules may include naturally occurring proteins, synthetic proteins, mutated proteins, fusion proteins or chimeric proteins. The proteins or peptides may be chemically synthesized. In some embodiments, the proteins or peptides may be naturally synthesized in a cell. In some embodiments, the biomolecules are recombinant proteins or peptides that may be isolated from cells or tissue section. The biomolecules may include post translationally modified proteins or peptides. The proteins may comprise enzymes or catalyst. The proteins, peptides or amino acids may be isolated from various sources, such as a bacterial source, an animal source or a human source.

Example 1

Preparation of Paper Substrate

Reagents: 31-ETF was from GE Healthcare. Paper substrates were impregnated with melezitose and other reagents by dipping cellulose paper (Whatman 31ETF) in warmed solutions of the appropriate formulations followed by drying the substrate using line oven conveyors. The dried substrates were then sealed in Mylar bags with dessicant until further testing. Four dipping formulations were prepared: (1) a 15% (on a weight-per-volume basis) melezitose solution, (2) a standard FTA solution also containing 15% melezitose. The standard FTA components comprise the following (on a weight-per-volume basis): 0.24% EDTA, 1.63% sodium dodecyl sulfate (SDS), 1.61% Tris buffer salt, and 0.56% Uric acid, (3) a 5% (on a weight-per-volume basis) Ficoll PM400, and (4) a solution contained the following percent sub-components: 6.5% melezitose, 4.2% Ficoll PM 70, and 4.2% Ficoll PM400, referred to hereinafter as melezitose-Ficoll formulation.

Example 2

Protein Stability Assay

Three proteins were selected for initial stability evaluation on cellulose-based substrates: the cytokine IL-8, the cholesterol protein Apolipoprotein B (ApoB), and the enzyme β-galactosidase (β-gal). IL-8 was selected as it is a representative biomarker for respiratory infection. ApoB was selected as a model labile protein (i.e. known short half-life on dried blood spots). β-gal was selected as a third model protein for its ability to provide direct quantification of enzymatic activity.

For the evaluation of each substrate formulation, 3 mm punches of the substrates were individually spotted with 3 μL of buffer or citrate-phosphate-dextrose (CPD)-stabilized human blood spiked with the protein of interest. The spike concentrations used were: 0.1 mg/mL for Apo B, 3.3 ng/mL for IL-8 and 10 μg/mL for β-gal. The spotted samples were then dried and stored in a low humidity environment. For ApoB and IL-8, proteins were eluted off by adding an elution buffer, and the substrate was incubated under continuous shaking. The eluted protein was then detected using a commercial ELISA kit. For β-gal, protein stability was determined using two different methods. In the first method, the protein was eluted from each substrate into an elution buffer and the activity of the eluted protein was measured. In the second method, a punch of each substrate was placed directly in analysis buffer and the enzymatic activity 'on-paper' was analyzed. With buffered samples, β-gal activity was assessed by the conversion of the colorless substrate o-nitrophenyl galactoside to the yellow product o-nitrophenol. With blood samples, β-gal activity was assessed by the conversion of the substrate with chlorophenol red galactopyranoside (CPRG) to chlorophenol red. In later studies, other proteins including IL-1β, IL-6, and TNF-α, were processed and analyzed in a manner similar to IL-8, as described above.

The stability of protein in dried blood spot was determined after long-term storage at room temperature using 31-ETF cellulose dip-coated in an FTA™ solution or in a solution of FTA™+15% melezitose, and the relative stability data from both substrates are shown in Table 1. The data were normalized to the signal of each protein analyte on or eluted off from unmodified 31-ETF™ cellulose. Table 1 clearly demonstrates that inclusion of melezitose in either dipping formulation unexpectedly resulted in improved analyte signal relative to either 31-ETF™ cellulose or FTA™ substrate. Although the magnitude of signal improvement is somewhat protein dependent, the highest signal was achieved for the substrate comprising FTA™+15% melezitose for each analyte in this example. Melezitose-containing substrates show a minimum of 20-60% improvement in signal for eluted proteins when compared to proteins eluted from unmodified 31-ETF™ after at least a month of sample storage at ambient temperatures ranging from ~20-22° C. (Table 1). Days of storage are denoted in parentheses and % improvement was calculated as: (signal for test paper–signal for 31ETF)/(signal for 31ETF)*100.

TABLE 1

Change in protein signal relative to unmodified 31-ETF ™ ceullulose after prolonged room temperature storage:

| Proteins | Assay | % Change with FTA + 15% melezitose | % Change with FTA |
|---|---|---|---|
| Apo B | ELISA | +29 (46) | −27 (46) |
| β-gal | Enzyme activity (on paper) | +23 (60) | −46 (60) |
| β-gal | Enzyme activity (eluted) | +17 (60) | −40 (60) |
| IL-8 | ELISA | +64 (60) | +50 (60) |

The FTA™ substrate contains denaturants, such as SDS, which results in negative values for % change in protein signal relative to 31-ETF™ for some analytes, as shown in Table 1. Unexpectedly, impregnating trisaccharides, such as melezitose, into the substrate results in improved detection signal (net positive values) in the presence of SDS during room temperature sample storage, thereby demonstrating enhanced protein stability relative to FTA™ without melezitose.

Example 3

Protein Stability at 30° C.

A list of formulations was selected for determining protein stability after long-term (90-day) sample storage. In this example, human blood samples containing analyte of interest were applied to each substrate, and stored for 90 days at 30° C. under low humidity conditions, and then protein stability was determined as described in Example 2. All substrates were prepared as described above in Example 1. Punches of the substrate formulations were individually dosed with IL-1β (6 pg/μL), IL-8 (7.5 ng/mL), TNF-α (8 pg/μL), or β-gal (10 μg/mL) in blood and dried at room temperature as described above. Dried blood spots from the selected substrates were compared with unmodified 31-ETF cellulose after long-term storage (days of storage in parentheses) at 30° C.

Based on ELISA or enzymatic activity data, the stabilizing effects of melezitose-containing substrates varied with the types of protein analytes tested, however, all the analytes showed improved signal on substrates containing melezitose relative to 31-ETF cellulose (Table 2). For example, after 90 days of storage, the eluted IL-1β signal was 24% greater for the substrate containing 15% melezitose and 52% greater for the substrate containing melezitose-Ficoll formulation than the corresponding signal from the unmodified 31-ETF. The net improvement in signal for melezitose-containing substrate relative to 31-ETF cellulose after long-term storage at 30° C. is shown in Table 2. Though 5% Ficoll PM400 alone provided a stabilizing effect for some proteins such as, IL-0, IL-8, TNF-α, and β-gal as investigated herein, the substrates with melezitose-Ficoll formulation which comprises melezitose in combination with Ficoll (or similar compositions as of Ficoll) showed superior stabilizing effects, as shown in Table 2. In Table 2, the days of storage for all dried blood spot samples are shown in parentheses and % improvement calculated as: (test paper−31ETF)/(31ETF)*100.

TABLE 2

Improvement in signal for melezitose-containing substrate relativeto 31-ETF cellulose after long-term storage at 30° C.

| | | % Improvement with | | |
|---|---|---|---|---|
| Protein | Assay | melezitose-Ficoll formulation (days) | 5% Ficoll PM-400 (days) | 15% melezitose (days) |
| IL-1 β | ELISA | +52 (91) | +31 (91) | +24 (91) |
| IL-8 | ELISA | +52 (90) | +8 (90) | +34 (90) |
| TNF-α | ELISA | +14 (91) | −10 (91) | +23 (91) |
| β-gal | Enzymatic activity (on paper) | +63 (90) | +47 (90) | +49 (90) |
| β-gal | Enzymatic activity (eluted) | +181 (90) | +186 (90) | +127 (90) |

Example 4

Elution Efficiency of β-Gal from Dried Samples

ELISA signal for cytokine targets (IL-1β, IL-8, and TNF-α) and ApoB provided a useful measure of the relative stabilizing effects of different cellulose substrates. When the analyte signal is suppressed, it is difficult to determine whether the suppressed signal results from complete elution coupled with a substantial protein denaturation or incomplete elution of substantially active, non-denatured proteins. Since β-gal signal is necessarily dependent on the active protein, this particular analyte provided an opportunity to measure the actual elution efficiency of active, non-denatured protein by comparing the "on-paper" signal with the eluted signal.

β-gal spiked blood samples were prepared as above and the stability of proteins was determined for long-term storage in a manner identical to Example 3. The samples were thus spotted onto 3 mm substrate punches, dried, and stored at 30° C. under low humidity condition. The samples were stored for 14-90 days, and approximately 50% elution improvement was consistently observed across this storage interval, as shown in FIG. 1. Each data point of FIG. 1 represents the ratio of eluted-to-total ("on-paper") signal of active protein as determined by a colorimetric enzymatic activity assay. Elution conditions were achieved by placing a 3 mm dried blood spot sample into a microcentrifuge tube with 100 mL buffer (PBS/0.05% Tween-20) and mixed thoroughly (800 rpm, 1 h) before determining the elution efficiency. FIG. 1 shows the enhanced elution efficiency of active, non-denatured β-gal when recovered from a substrate with 15% melezitose relative to unmodified 31-ETF cellulose when measured in this manner.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A method for extracting, stabilizing and eluting a protein or peptide from a biological sample disposed on a non-dissolvable dry solid substrate, wherein the non-dissolvable dry solid substrate comprises cellulose, cellulose acetate or glass fiber, or a combination thereof, and wherein the non-dissolvable dry solid substrate is a melezitose-impregnated solid substrate that is prepared by dipping the substrate in a melezitose solution having a melezitose concentration in a range of 10% to 30% on a weight per volume basis, the method comprising:
   contacting the biological sample to the melezitose-impregnated solid substrate without solubilizing the melezitose-impregnated solid substrate;
   drying the biological sample to a water content of less than 2%; and
   eluting the a protein or peptide from the biological sample dried on the melezitose-impregnated solid substrate by rehydrating the melezitose-impregnated solid substrate in an elution buffer.

2. The method of claim 1, wherein the melezitose-impregnated solid substrate provides 70 to 90% recovery of the protein or peptide from the substrate.

3. The method of claim 1, wherein the melezitose-impregnated solid substrate elutes the protein or peptide in an intact form.

4. The method of claim 1, wherein the melezitose-impregnated solid substrate comprises cellulose.

5. The method of claim 1, wherein the melezitose-impregnated solid substrate is prepared by dipping the substrate in a melezitose solution having a melezitose concentration of 15% on a weight per volume basis.

6. The method of claim 1, wherein the melezitose-impregnated solid substrate further comprises one or more lysis reagents, nucleic acid denaturing reagents and combinations thereof.

7. The method of claim 6, wherein the lysis reagent is selected from thiocyanate salts, detergents, urea or combinations thereof.

8. The method of claim 6, wherein the lysis reagent is selected from guanidinium thiocyanate, sodium thiocyanate, sodium dodecyl sulfate (SDS), arginine, urea or combinations thereof.

9. The method of claim 1, wherein the melezitose-impregnated solid substrate further comprises a polysaccharide selected from dextran, ficoll, chitosan, amylopectin, alginate, carboxymethyl cellulose or combinations thereof.

10. The method of claim 9, wherein the polysaccharide is ficoll.

11. The method of claim 9, wherein the melezitose-impregnated solid substrate further comprises 1 to 10% ficoll.

12. The method of claim 1, wherein the melezitose-impregnated solid substrate further comprises reducing agents, buffers, anti-oxidants, chelating agents or combinations thereof impregnated therein.

13. The method of claim 12, wherein the reducing agent is selected from dithiothreitol (DTT), 2-mercaptoethanol (2-ME), tris(2-carboxyethyl)phosphine (TCEP) or combinations thereof.

14. The method of claim 12, wherein the buffer is selected from 2-Amino-2-hydroxymethyl-propane-1,3-diol (Tris), 2-(N-morpholine) ethanesulfonic acid (MES), 3-(N-morpholino) propanesulfonic acid (MOPS), citrate buffers, 4-(2-hydroxyethyl)-1-piperazineethanesulfonic acid (HEPES), phosphate buffers or combinations thereof.

15. The method of claim 12, wherein the chelating agent is selected from ethylenediaminetetraacetic acid (EDTA), citric acid, ethylene glycol tetraacetic acid (EGTA), or combinations thereof.

\* \* \* \* \*